(12) United States Patent
Barkow et al.

(10) Patent No.: US 7,308,075 B2
(45) Date of Patent: Dec. 11, 2007

(54) METHOD AND APPARATUS FOR ADJUSTING A SCANNING REGION IN A COMPUTED TOMOGRAPHY SYSTEM

(75) Inventors: Kerstin Barkow, Neuss (DE); Robert Kagermeier, Nürnberg (DE); Johannes Paschold, Rudolstadt (DE)

(73) Assignee: Siemens Aktiengesellschaft, Munich (DE)

( * ) Notice: Subject to any disclaimer, the term of this patent is extended or adjusted under 35 U.S.C. 154(b) by 201 days.

(21) Appl. No.: 11/202,711

(22) Filed: Aug. 11, 2005

(65) Prior Publication Data

US 2006/0034421 A1 Feb. 16, 2006

(30) Foreign Application Priority Data

Aug. 16, 2004 (DE) .................. 10 2004 039 683

(51) Int. Cl.
*G01N 23/083* (2006.01)
(52) U.S. Cl. ......................................... 378/20; 378/205
(58) Field of Classification Search .................... 378/4, 378/20, 205, 208–209
See application file for complete search history.

(56) References Cited

U.S. PATENT DOCUMENTS

| | | | | |
|---|---|---|---|---|
| 6,460,206 | B1 * | 10/2002 | Blasche et al. ................. | 5/601 |
| 6,917,666 | B2 * | 7/2005 | Wollenweber ................ | 378/20 |
| 2002/0118280 | A1 | 8/2002 | Medlar et al. | |

FOREIGN PATENT DOCUMENTS

DE 101 09 219 A1 9/2002

* cited by examiner

*Primary Examiner*—Hoon Song
(74) *Attorney, Agent, or Firm*—Brinks, Hofer, Gilson & Lione

(57) ABSTRACT

A method and an apparatus are provided for adjusting a scanning region of a computed tomography (CT) scanner. At least one edge point of a set-point scanning region on a patient examination table associated with the CT scanner is indicated by hand signals of a user. Via a distance sensor, mounted at a reference point of the patient examination table, a distance from the at least of edge point to the reference point is measured. From the measured distance, the position of the at least one edge point relative to the patient examination table is determined, and a corresponding edge of a CT scanning region of the CT scanner is conformed to the derived position.

18 Claims, 2 Drawing Sheets

METHOD AND APPARATUS FOR ADJUSTING A SCANNING REGION IN A COMPUTED TOMOGRAPHY SYSTEM

FIELD

The present embodiments relate, in general, to medical imaging systems, and in particular, to a method and an apparatus for adjusting a scanning region in a computed tomography (CT) system.

BACKGROUND

Generally, the terminology "CT scanner" is used when relating to a medical system that provides images of successive virtual slices of a region of a body of a patient to be examined, such as a computed tomography (CT) scanner or magnetic resonance (MRI) scanner.

Typically, prior to a computed tomography or CT examination of the patient, a scanning region is defined. As such, the terminology "scanning region" is, hereafter, used for the region of the body of the patient to be examined, or a region of a patient examination table corresponding to that region of the patient body that is to be "scanned" in the course of the examination by successive imaging of successive slices of the patient body.

The scanning region is defined based on a topographic image made in a preliminary phase of the CT examination. Via a computer workstation located remotely from the patient, the targeted scanning region is selected in the topographic image via a suitable position-inputting device, such as a mouse, trackball, or the like.

In order to produce the topographic image, the patient is exposed to an irradiation load from an X-ray source. It would furthermore be desirable to be able to adjust the scanning region with the patient in relative proximity.

BRIEF SUMMARY

The present invention is defined by the appended claims. This description summarizes some aspects of the present embodiments and should not be used to limit the claims.

A method for adjusting the scanning region can be performed by relatively simple mechanisms and is relatively simple to use. A suitable apparatus for performing the method can be realized by the relatively simple mechanisms.

A user or an operator, such as a radiologist, is at or in the vicinity of a patient examination table associated with the CT scanner and hence close to the patient. The user may indicate at least one edge point of a scanning region (or set-point scanning region) to be adjusted using hand signals. The terminology "hand signal" is used, hereafter, for gestures the user makes with his bare hand or using a pointer device, such as a ladle, plate, or the like. The apparatus intended for performing the method is now configured for automatically determining a position of the indicated edge point. In other words, the position of the user's hand or the pointer relative to the patient examination table and for adapting a corresponding edge of the scanning region is used to adjust the CT scanner to the determined position.

A distance of the edge point indicated by hand signals is measured from at least one reference point of the patient examination table, and from the measured distance, the position of the edge point relative to the patient examination table is derived. For such distance measurement, the apparatus has at least one distance sensor, disposed at the at least one reference point or other location so as to be stationary relative to the patient examination table. Such distance sensor can measure the distance from the indicated edge point by transit time measurement or triangulation by using infrared or laser technology is commercially available and relatively inexpensive.

By the above-described method and the associated apparatus, adjusting the scanning region while close to the patient is enabled by simple mechanisms while also minimizing a risk of an incorrect adjustment of the scanning region. Moreover, the method is relatively simple to use and saves time, which is increasingly significant from the standpoint of economy in clinical procedures.

Expediently, such a distance measurement is made parallel to a long edge, oriented toward the user, of the patient examination table. The at least one distance sensor intended for the distance measurement is disposed on a longitudinal end, used as a reference point, of the patient examination table.

A use of a plurality of distance sensors at different reference points, such as at both longitudinal ends, diametrically opposite one another along the long edge, of the patient examination table can be provided as an option. As a result, the entire length of the patient examination table can be detected by measurement technology, even if relatively short-range distance sensors are used. Such distance sensors with typical ranges of approximately one meter are relatively inexpensive.

To increase the measurement precision and to avoid ambiguous distance measurement, which can occur in currently used distance sensors from close range because of the triangulation principle, connecting two distance sensors with different ranges at one reference point in parallel can also be advantageous.

In an advantageous feature of the proposed method, the user may indicate not only an edge point of the set-point scanning region toward the head but also an edge point toward the foot of the set-point scanning region. As such, the position relative to the patient examination table is determined at both edge points, and the actual scanning region of the CT scanner is adapted to the longitudinal region, formed between the two edge points, of the patient examination table.

Both from a hygienic standpoint and with a view to relatively fast and uncomplicated use of the method, the position of the indicated edge point can be determined in contact-less fashion. As such, in indicating the edge point, the user does not have to touch either the patient examination table or the apparatus. Alternately, however, a position specification that does involve contact may be used in the CT examination. In that case, the hand signal, indicating an edge point, on the part of the user includes touching or actuating a suitable touch-sensitive distance sensor, such as a linear potentiometer or the like.

To reliably minimize a mistakenly incorrect adjustment of the scanning region, the determined position of the edge point indicated by hand signals is reported back to the user via an optical signal. For this report back, the apparatus may include a display unit, which is configured relatively simply and inexpensively by a row of light emitting diodes extending along the long edge of the patient examination table. Alternately, a marking laser that reports the adjusted scanning region back via a light marking can be used as the display unit. In another alternate option for indicating the adjusted scanning region, the determined position of each indicated edge point can be identified by markings incorporated into a video image of the patient and the patient examination table that is visible to the user.

The adaptation of the scanning region of the CT scanner is not done until the user positively acknowledges and thus confirms the reported-back position of the indicated edge point, or every indicated edge point. As such, the apparatus may appropriately include a confirmation element, disposed on or in the vicinity of the patient examination table, which is configured as a confirmation key or the like.

Illustrative and exemplary embodiments of the invention are described in further detail below with reference to, and in conjunction with, the figures.

DETAILED DESCRIPTION

Figure 1:
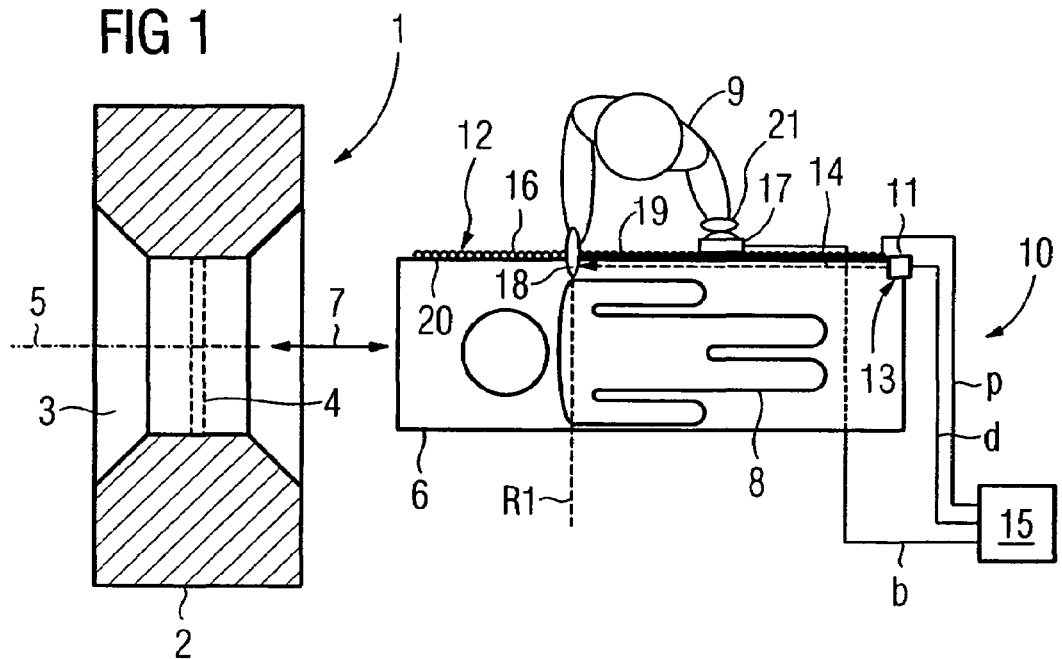
FIG. 1 illustrates, in a schematic top view, one embodiment of an apparatus for adjusting the scanning region of a CT scanner (shown in section), and a user adjusting an edge point, toward the head, of the scanning region.

Elements and sizes that correspond to one another are always identified by the same reference numerals throughout the drawings.

FIG. 1 shows a computed tomography scanner (hereinafter called CT scanner 1) in a schematic horizontal section. The CT scanner 1 includes a gantry 2 that is a substantially ring-shaped supporting frame. The gantry 2 has a central tunnel 3 about which an X-ray detector unit (not shown in detail) is rotatably supported, so that from different projections, X-rays of a slice-like three-dimensional volume, hereinafter called the imaging plane 4, can be made. The imaging plane 4 is located in this example substantially centrally in the interior of the tunnel 3 and perpendicular to the axis 5 of the tunnel 3.

Figure 2:
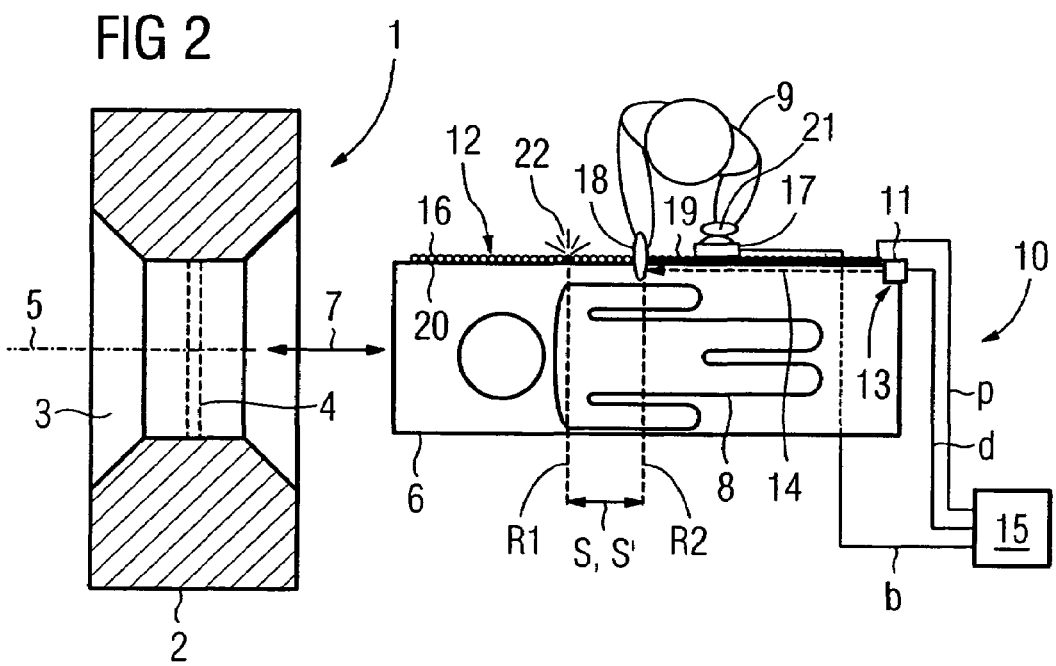
FIG. 2, in a top view corresponding to FIG. 1, illustrates schematically the user in the ensuing adjustment of the edge point, toward the foot, of the scanning region.

The CT scanner 1 further includes a table- or cot-like patient examination table 6, which can be driven into the tunnel 3 in an introduction direction 7 for the CT examination. FIGS. 1 and 2 show the patient examination table 6 in a fully retracted position out of the tunnel 3, and with a patient 8 lying on it.

During the course of the CT examination, the patient examination table 6, with the patient 8 lying on it, is introduced into the tunnel 3 of the gantry 2 in such a way that a region to be examined of the body of the patient 8 is located at the axial height of the imaging plane 4. Next, in a varying radial orientation of the X-ray detector unit (not shown) about the axis 5, X-rays of the imaging plane 4 and of the body tissue located in it are taken and put together in the computer to produce a gray-scale image of a slice of the body. Images of regions of the body of the patient 8, whose axial length exceeds the axial thickness of the imaging plane 4, are produced by varying or moving the axial position of the patient examination table 6 relative to the gantry 2 in increments. Adjoining or successive images of slices of the body of the patient 8 are taken. These individual successive slices are assembled in a computer to produce a three-dimensional image of the patient's body.

The procedure described above of the incrementally completed change in position of the patient examination table 6 relative to the gantry 2, each increment correspondingly taking a picture of a further slice of the body, is known as a "scan". For performing such a scan, an associated scanning region S is determined to define the axial positioning of the patient examination table 6 relative to the imaging plane 4 at which first and last images in an ongoing series of adjoining successive slice images are to be taken. With respect to the patient examination table 6 or the patient 8, the scanning region S may have one edge R1 toward the head of the patient to be examined and one edge R2 toward the patient's foot. Within the scope of this description, a formal distinction is made between the term set-point scanning region S', that is, the scanning region S that is to be adjusted in the course of the method described below, and the term CT scanning region S", that is, the scanning region S that is specified as a process parameter to the CT scanner 1.

To enable a user 9, such as a radiologist, to adjust the scanning region S in proximity to the patient, intuitively, and quickly, an apparatus 10 for adjusting the scanning region S is assigned to the patient examination table 6. The apparatus 10 includes a distance sensor 11, which is mounted, flanking a long edge 12, on the patient examination table 6 in the region of one longitudinal end 13 of the patient examination table 6. The distance sensor 11 is a commercially available optical distance meter, which by infrared or laser technology determines the distance of an object, located in the direction of a measuring beam 14, by transit time measurement or by using a triangulation method. The distance sensor 11 is oriented relative to the patient examination table 6 in such a way that the measurement beam 14 extends parallel to the long edge 12.

The apparatus 10 further includes an evaluation module 15, which can be a software component of a system controller (not further shown) of the CT scanner 1. A measurement signal d, which corresponds to a measured distance between the distance sensor 11 and a detected object, is sent to the evaluation module 15 by the distance sensor 11.

The apparatus 10 further includes a display unit 16, in the form of a strip of light emitting diodes, extending along the long edge 12, that is triggered from the evaluation module 15 by a control signal p.

The apparatus 10 furthermore includes a key 17, mounted on the long edge 12 of the patient examination table 6, as a confirmation element. The key 17 is connected to the evaluation module 15 for forwarding a confirmation signal b.

For defining and changing the scanning region S, the user 9 approaches the long edge 12 of the patient examination table 6, and thus directly approaches the patient 8 lying on it, and indicates an edge point R1 or R2 of the set-point scanning region S' by putting one hand 18, optionally with the aid of a pointer, such as a ladle, plate, a sheet of paper, and so forth, at the targeted axial height of the patient examination table 6 above the long edge 12 and thus keeps it in the measurement beam 14 of the distance sensor 11. The distance sensor 11 here determines the distance of the hand 18 (or pointer) from the longitudinal end 13 to which the distance sensor 11 is secured, and sends the corresponding measurement signal d to the evaluation module 15.

The evaluation module 15 uses the location where the distance sensor 11 is mounted relative to the patient examination table 6 (that is, in the present case, the longitudinal end 13), as a reference point. From this reference point and the measured value, the evaluation module 15 calculates the axial position that the indicated edge point R1 or R2 may occupy relative to the patient examination table 6. For reporting the calculated position back to the user 9, the evaluation module 15 triggers the display unit 16 such that all the light emitting diodes 19 of the display unit 16 that are located between the distance sensor 11 and the calculated position of the hand 18 are activated, while the light emitting diodes 20 of the display unit 16 that are located toward the head from that position are deactivated. The user 9 is thus provided an optical feedback signal, on the basis of which he can check whether the edge point R1 or R2 in the set-point scanning region S' that he has indicated has been correctly detected by the evaluation module 15.

In the affirmative, the user 9 actuates the key 17 with his other hand 21 and thus, by outputting the confirmation signal b to the evaluation unit 15, positively acknowledges the determined position of the indicated edge point R1 or R2. Upon receiving the confirmation signal, the evaluation unit 15 adopts the determined position of the edge point R1 or R2.

For a substantially complete determination of the scanning region S, the two edge points R1 and R2 are defined, as shown in FIGS. 1 and 2. FIG. 1 schematically shows the determination of the edge point R1 toward the head of the patient as a first edge point. FIG. 2 shows an ensuing second method step, in which the user 9 specifies the edge point R2 toward the foot of the patient as a second edge point. From FIG. 2, the evaluation module 15, by corresponding triggering of the display unit 16, may further indicate the already-determined position of the edge point R1 toward the head of the patient as an aid in orientation during the adjustment of the second edge point R2, because a light emitting diode 22 is triggered, corresponding to that position, in a way that contrasts with the light emitting diodes 20 surrounding it.

Once the user 9 has positively acknowledged the second edge point R2, by pressing the key 17 again, the evaluation module 15 determines what is now the scanning region S as the axial region of the patient examination table 6 located between the defined edge points R1 and R2, and forwards this scanning region S as a CT scanning region S" to the system controller of the CT scanner 1. The edge points R1 and R2 continue to be indicated, as shown in FIG. 3, as an orientation aid for the user 9 as a result of triggering of the corresponding light emitting diodes 20.

Via the CT scanning region S", stored in memory in the system controller of the CT scanner 1, during the examination the acquisition of data is performed only within the region of the body of the patient 8 that is located between the edge points R1 and R2.

Figure 3:
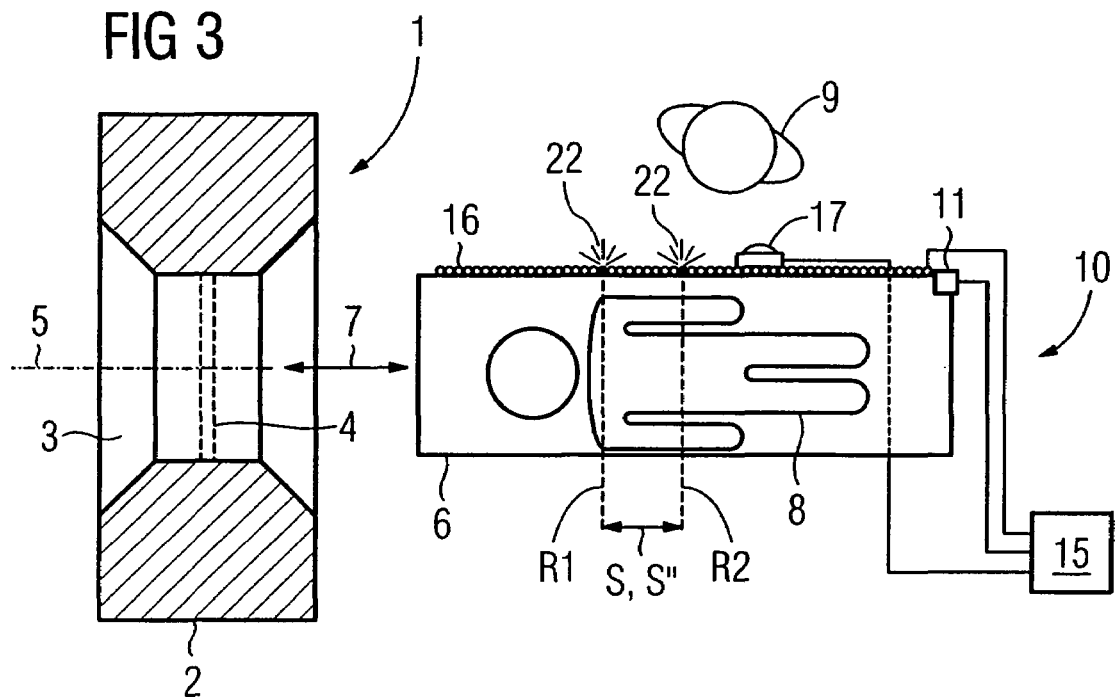
FIG. 3, in a top view corresponding to FIG. 1, illustrates schematically the apparatus and the user once the adjustment of the scanning region has been performed.

Moreover, the user 9, via a predetermined actuation pattern of the key 17, such as holding down the key 17 for a predetermined actuation time, can erase the CT scanning region S" and the defined edge points R1 and R2, in order to begin anew to adjust the scanning region S again in the order shown in FIGS. 1 through 3.

Figure 4:
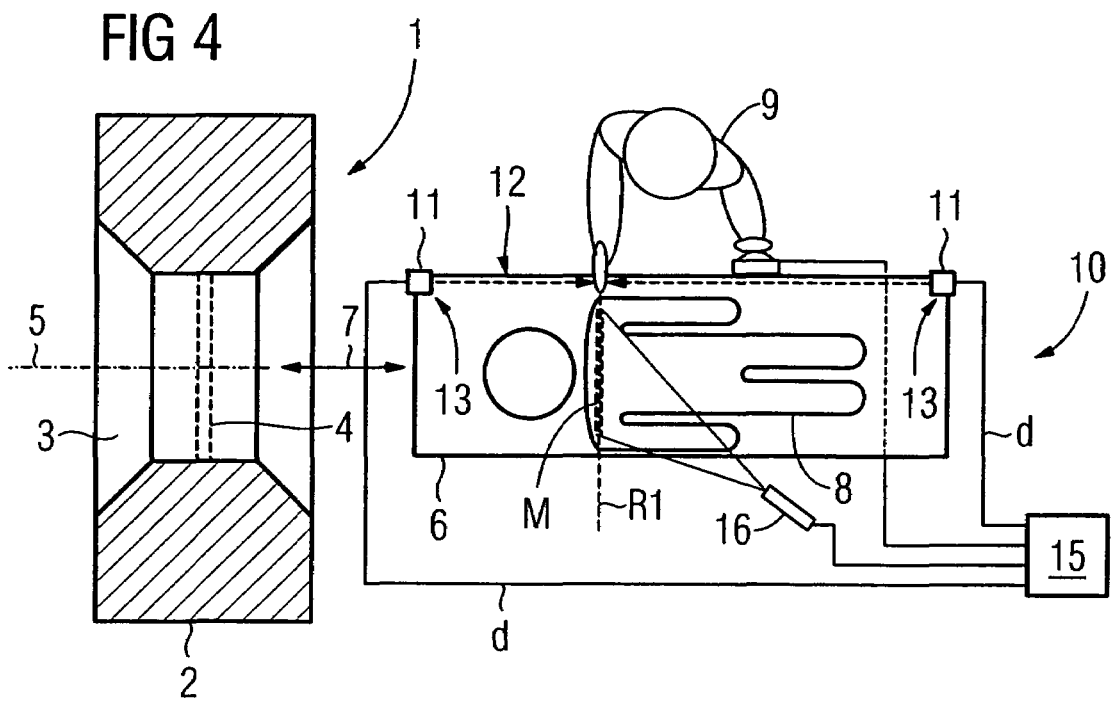
FIG. 4, in a top view corresponding to FIG. 1, illustrates schematically an alternate apparatus for adjusting the scanning region of a CT scanner.

In FIG. 4, an alternate example of the apparatus 10 is shown. For this alternate apparatus 10, two distance sensors 11 may be provided on a respective longitudinal ends 13 of the long edge 12. The measurement beams 14 of the two distance sensors 11 are oriented counter to one another along the long edge 12. Moreover, comparatively inexpensive commercial distance sensors 11 with a comparatively short range on the order of magnitude of one meter can be used, and because of the dual, contrary-direction configuration of the distance sensors 11, an adequate measurement length to substantially cover the entire long edge 12 is nevertheless attained. If distance meters operating on the basis of triangulation are used, then each distance sensor 11 includes two distance meters, disposed parallel to one another, each with a different range (such as 1 m and 30 cm), in order to avoid ambiguous measurement values d, which can occur when only a single such distance meter is used at a relatively close range.

The apparatus 10, shown in FIG. 4, can further include, instead of a row of light emitting diodes, a marking laser configured as the display unit 16. This laser is triggered by the evaluation module 15 so as to generate a light marking M at the point of the patient examination table 6 that corresponds to a position, determined by the evaluation module 15, of an edge point R1 or R2 indicated by the user 9.

The invention claimed is:

1. A method for adjusting a scanning region of a computed tomography (CT) scanner, the method comprising:
   determining at least one edge point of a set-point scanning region associated with the CT scanner via hand signals;
   measuring, via at least one distance sensor located relative to a reference point of a patient examination table, a distance from the at least one edge point to the reference point;
   determining, from the measured distance, a position of the at least one edge point relative to the patient examination table;
   determining a corresponding edge of a CT scanning region of the CT scanner via the determined position of the at least one edge point; and
   adjusting the scanning region.

2. The method according to claim 1, wherein a distance parallel to a long edge of the patient examination table from the at least one edge point to a longitudinal end of the patient examination table is determined as the reference point.

3. The method according to claim 1, wherein a first edge point, located toward a head of a patient, and a second edge point, located toward a foot of the patient, of the set-point scanning region are indicated, and the respective position of the first and second edge points is determined, and the CT scanning region is conformed to the longitudinal region of the patient examination table formed between the first and second edge points.

4. The method according to claim 1, wherein the position of the at least one edge point is determined in contact-less fashion.

5. The method according to claim 1, wherein the determined position of the at least one edge point is reported back to a user by an optical signal.

6. The method according to claim 5, wherein the determined position of the at least one edge point is accepted for the CT scanning region when the user acknowledges the reported-back position of the at least one edge point.

7. The method of claim 3, wherein the position of the at least one edge point is determined in contact-less fashion.

8. The method of claim 3, wherein the determined position of the at least one edge point is reported back to a user by an optical signal.

9. An apparatus for adjusting a scanning region of a computed tomography (CT) scanner, the apparatus comprising:
   at least one distance sensor associated with a reference point of a patient examination table, the at least one distance sensor positioned for measuring a distance of at least one edge point, indicated by hand signals of a user, of a set-point scanning region from the reference point; and an evaluation module operable to determine, from the distance, a position of the at least one edge point relative to the patient examination table and operable to conform a corresponding edge of a CT scanning region of the CT scanner to the at least one edge point.

10. The apparatus according to claim 9, wherein the at least one distance sensor comprises an infrared sensor.

11. The apparatus according to claim 9, wherein the at least one distance sensor comprises a laser sensor.

12. The apparatus according to claim 9, further comprising:

an optical display unit operable to report a determined position of the at least one edge point.

13. The apparatus according to claim 12, wherein the display unit comprises a row of light emitting diodes.

14. The apparatus according to claim 12, wherein the display unit comprises to a marking laser.

15. The apparatus according to claim 9, further comprising:

a confirmation element disposed on or in the vicinity of the patient examination table, the confirmation element operable to confirm the determined position of the at least one edge point.

16. The apparatus according to claim 12, further comprising:

a confirmation element disposed on or in the vicinity of the patient examination table, the confirmation element operable to confirm the determined position of the at least one edge point.

17. The apparatus according to claim 10, further comprising:

an optical display unit operable to report a determined position of the at least one edge point.

18. The apparatus according to claim 11, further comprising:

an optical display unit operable to report a determined position of the at least one edge point.

* * * * *